(12) United States Patent
Collins et al.

(10) Patent No.: US 10,799,340 B2
(45) Date of Patent: Oct. 13, 2020

(54) INTRAOCULAR LENS HAVING A CAPSULAR RING FOR INHIBITING CAPSULAR OPACIFICATION

(71) Applicant: NOVARTIS AG, Basel (CH)

(72) Inventors: Stephen Collins, Fort Worth, TX (US); Niranjana Nandakumar, Plano, TX (US); John Radle, Flower Mound, TX (US); Stephen Van Noy, Southlake, TX (US); Douglas B. Wensrich, Bedford, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 14/821,891

(22) Filed: Aug. 10, 2015

(65) Prior Publication Data

US 2017/0042667 A1    Feb. 16, 2017

(51) Int. Cl.
*A61F 2/16*         (2006.01)

(52) U.S. Cl.
CPC .. *A61F 2/1694* (2013.01); *A61F 2002/16901* (2015.04); *A61F 2210/0057* (2013.01); *A61F 2220/00* (2013.01); *A61F 2220/0008* (2013.01)

(58) Field of Classification Search
CPC ................ A61F 2/1613; A61F 2/1648; A61F 2002/169; A61F 2002/16901; A61F 2002/16902; A61F 2/1694
See application file for complete search history.

(56) References Cited

U.S. PATENT DOCUMENTS

| 5,628,795 | A  | * | 5/1997 | Langerman | ............... A61F 2/14 623/4.1 |
| 8,734,510 | B2 | * | 5/2014 | Bernard | ............... A61F 2/1613 623/6.16 |
| 9,095,424 | B2 |   | 8/2015 | Kahook et al. | |
| 9,125,736 | B2 |   | 9/2015 | Kahook et al. | |
| 9,289,287 | B2 |   | 3/2016 | Kahook et al. | |
| 9,364,316 | B1 |   | 6/2016 | Kahook et al. | |
| 9,387,069 | B2 |   | 7/2016 | Kahook et al. | |

(Continued)

FOREIGN PATENT DOCUMENTS

| EP | 0337390 A2 * | 10/1989 | ........... A61F 2/1613 |
| EP | 0779063 A1   | 6/1997  | |

(Continued)

OTHER PUBLICATIONS

PCT/IB2016/052511, International Search Report, International Searching Authority, dated Jul. 15, 2016, 4 pgs.

*Primary Examiner* — Leslie Lopez

(57) ABSTRACT

An IOL system includes a capsular ring having a concave exterior surface extending around its circumference that is configured, upon insertion into a capsular bag of a patient's eye, to engage an equatorial region of the capsular bag. The concave exterior surface extends between an anterior surface and a posterior surface of the capsular ring. A first one or more flaps are arranged on the anterior surface such that at least a portion of each of the first one or more flaps, upon insertion into the capsular bag of a patient's eye, engages an anterior portion of the capsular bag. Similarly, a second one or more flaps are arranged on the posterior surface such that at least a portion of each of the second one or more flaps, upon insertion into a capsular bag of a patient's eye, engages a posterior portion of the capsular bag.

12 Claims, 6 Drawing Sheets

(56) References Cited

U.S. PATENT DOCUMENTS

| | | |
|---|---|---|
| 9,421,088 B1 | 8/2016 | Kahook et al. |
| 2005/0177230 A1* | 8/2005 | Young .................... A61F 2/16 623/6.16 |
| 2010/0204788 A1 | 8/2010 | Van Noy |
| 2014/0172089 A1* | 6/2014 | Lee ..................... A61F 2/1694 623/6.12 |
| 2015/0216652 A1* | 8/2015 | Jansen ................. A61F 2/1613 623/6.43 |
| 2015/0230981 A1 | 8/2015 | Kahook et al. |
| 2016/0235587 A1 | 8/2016 | Kahook et al. |
| 2016/0278912 A1 | 9/2016 | Kahook et al. |

FOREIGN PATENT DOCUMENTS

| | | |
|---|---|---|
| JP | 05-058118 U | 8/1993 |
| WO | 200164136 A2 | 9/2001 |
| WO | 2007082342 A1 | 7/2007 |

* cited by examiner

INTRAOCULAR LENS HAVING A CAPSULAR RING FOR INHIBITING CAPSULAR OPACIFICATION

FIELD

This present disclosure relates generally to the intraocular lenses (IOLs) and, more particularly, to an IOL having a capsular ring for inhibiting capsular opacification.

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). FIG. 1 is a diagram of an eye 100 illustrating anatomical structures related to the surgical removal of a cataract and the implantation of an IOL. The eye 100 comprises an opacified lens 102, an optically clear cornea 104, and an iris 106. A lens capsule (capsular bag 108) located behind the iris 106 of the eye 100 contains the opacified lens 102. More particularly, the opacified lens 102 is seated between an anterior capsule segment (anterior capsule 110) and a posterior capsular segment (posterior capsule 112). The anterior capsule 110 and the posterior capsule 112 meet at an equatorial region 114 of the capsular bag 108. The eye 100 also comprises an anterior chamber 116 located in front of the iris 106 and a posterior chamber 118 located between the iris 106 and the vitreous body.

A common technique for cataract surgery is extracapsular cataract extraction ("ECCE"), which involves the creation of an incision near the outer edge of the cornea 104 and an opening in the anterior capsule 110 (i.e., an anterior capsulotomy) through which the opacified lens 102 is removed. The lens 102 can be removed by various known methods. One such method is phacoemulsification, in which ultrasonic energy is applied to the lens to break it into small pieces that are aspirated from the capsular bag 108. Thus, with the exception of the portion of the anterior capsule 110 that is removed in order to gain access to the lens 102, the capsular bag 108 may remain substantially intact throughout an ECCE. The intact posterior capsule 112 provides a support for the IOL and acts as a barrier to the vitreous humor within the posterior chamber 120 of the eye 100. Following removal of the opacified lens 102, an artificial IOL, which may be designed to mimic the transparency and refractive function of a healthy lens, is typically implanted within the capsular bag 108 through the opening in the anterior capsule 110. The IOL may be acted on by the zonular forces exerted by a ciliary body 122 and attached zonules 124 surrounding the periphery of the capsular bag 108. The ciliary body 122 and the zonules 124 anchor the capsular bag 108 in place and facilitate accommodation, the process by which the eye 100 changes optical power to maintain a clear focus on an image as its distance varies.

A frequent complication of ECCE and other forms of cataract surgery is opacification of the posterior capsule 112. Posterior capsule opacification ("PCO") results from the migration of residual lens epithelial cells from the equatorial region 114 of the capsular bag 108 toward the center of the posterior capsule 112. One factor contributing to the development of PCO is contact between the IOL and the surface of the posterior capsule 112. Subsequent to ECCE, the lens epithelial cells may proliferate between the IOL and the surface of the posterior capsule 112, leading to wrinkling and clouding of the normally clear posterior capsule 112. If clouding of the posterior lens capsule 112 occurs within the visual axis, then the patient will experience a decrease in visual acuity and may require additional surgery to correct the patient's vision.

A widely utilized procedure to clear the visual axis of PCO is Neodymium: Yttrium-Aluminum-Garnet ("Nd/YAG") laser capsulotomy, in which a laser beam is used to create an opening in the center of the cloudy posterior capsule 112. However, Nd/YAG laser capsulotomy exposes patients to the risk of severe complications that can lead to significant visual impairment or loss, such as retinal detachment, papillary block glaucoma, iris hemorrhage, uveitis/vitritis, and cystoid macula edema. Moreover, the laser energy is ordinarily directed though the IOL, which may damage the optics of the implant or disrupt its placement within the capsular bag 108. Accordingly, there exists a need to prevent the occurrence of PCO rather than treating PCO at a later date after implantation of an IOL.

SUMMARY

In general, the present disclosure relates to an IOL system designed to inhibit PCO. In certain embodiments, a capsular ring of the IOL system described herein includes a capsular ring having a concave exterior surface extending around its circumference that is configured, upon insertion into a capsular bag of a patient's eye, to engage an equatorial region of the capsular bag. The concave exterior surface extends between an anterior surface and a posterior surface of the capsular ring. A first one or more flaps are arranged on the anterior surface such that at least a portion of each of the first one or more flaps, upon insertion into the capsular bag of a patient's eye, engages an anterior portion of the capsular bag. Similarly, a second one or more flaps are arranged on the posterior surface such that at least a portion of each of the second one or more flaps, upon insertion into a capsular bag of a patient's eye, engages a posterior portion of the capsular bag.

Certain embodiments of the present disclosure may provide one or more technical advantages. For example, embodiments of the present disclosure may provide users (i.e., surgeons) with an atraumatic tool to block the proliferation and migration of lens epithelial cells across the inner surface of the lens capsule (i.e., the inner surfaces of both the anterior and posterior capsules). As a result, embodiments of the present disclosure may prophylactically treat PCO and thus reduce the need for post-operative posterior capsulotomy. Accordingly, complications associated with post-operative posterior capsulotomy (e.g., damage to the IOL) may be avoided. Additionally, prophylactically treatment of PCO may reduce the number of surgical procedures the patient needs to undergo, thereby reducing the trauma and cost to the patient. May have otherwise had to undergo.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
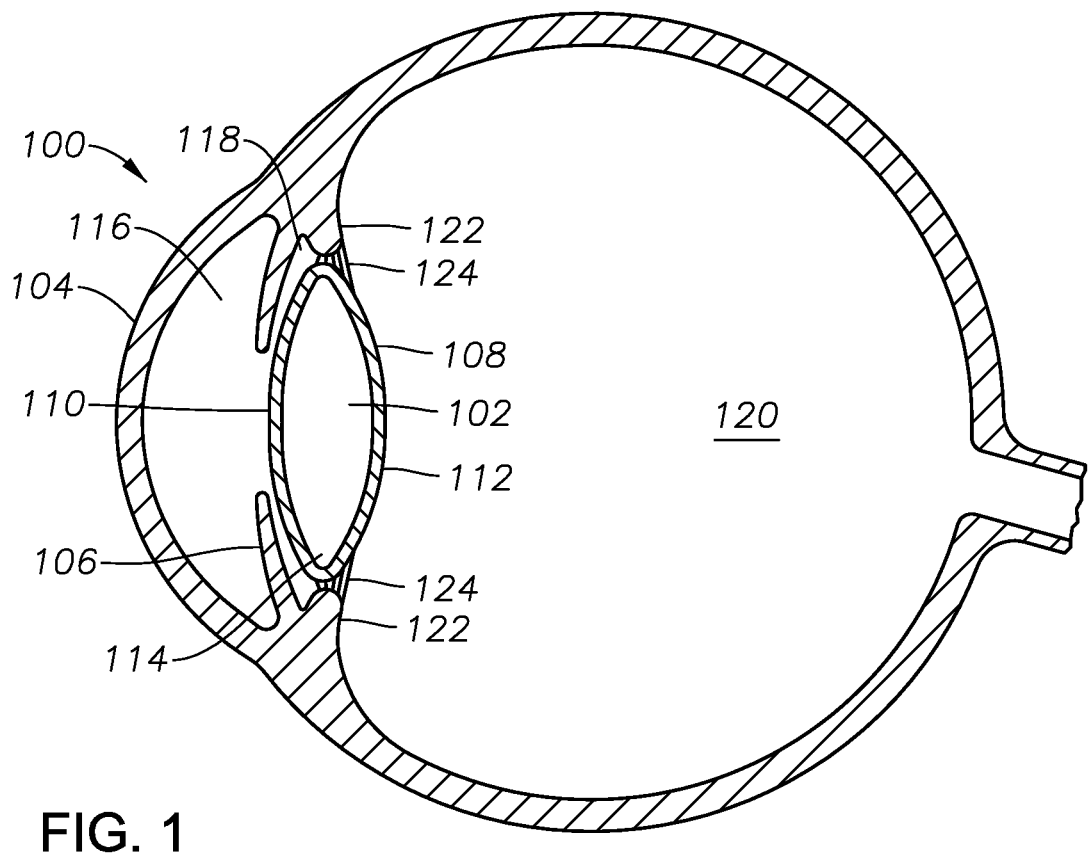
FIG. 1 is a diagram of an eye illustrating anatomical structures related to the surgical removal of a cataract and the implantation of an IOL.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure relates to an IOL system designed to inhibit PCO. In some instances, embodiments of the present disclosure comprise capsular ring configured to be inserted into the capsular bag of a patient's eye. Once inserted, the capsular ring may keep the capsular bag open, thereby facilitating circulation of aqueous humor into the capsular bag. In addition, the periphery of the capsular ring may be designed to engage the equatorial region of the capsular bag in a manner that inhibits migrations of lens epithelial cells from the equatorial region. Both circulation of aqueous humor and inhibition of epithelial cell migration may inhibit capsular opacification.

Figure 2A:
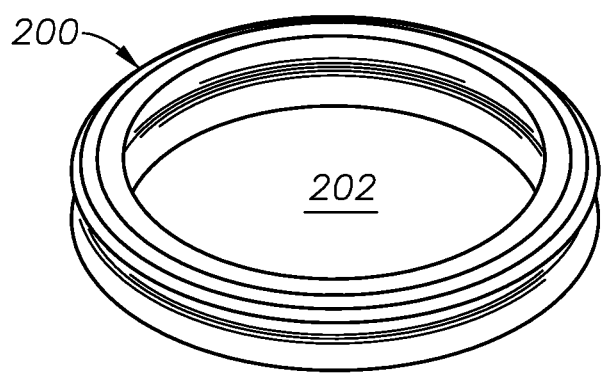
FIGS. 2A-2B illustrate an exemplary capsular ring, according to certain embodiments of the present disclosure.
Figure 2B:
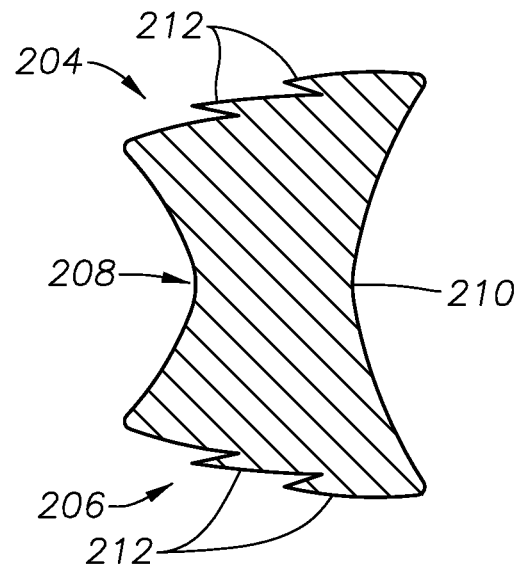

FIGS. 2A-2B illustrate an exemplary capsular ring 200, according to certain embodiments of the present disclosure. Capsular ring 200, when in the depicted expanded (i.e., unstressed) position, defines a generally circular central opening 202. Capsular ring 200 may be defined by an anterior surface 204 and a posterior surface 206, and anterior surface 204 and posterior surface 206 may be connected on one side by an exterior surface 208 and on the other side by an interior surface 210. In other words, anterior surface 204, posterior surface 206, exterior surface 208, and interior surface 210 may collectively define the cross-sectional shape of capsular ring 200. As used herein, the terms "anterior" and "posterior" refer to the positioning of the surfaces after capsular ring 200 has been inserted into the capsular bag 108 of a patient's eye. However, because capsular ring 200 may be symmetrical (i.e., in cross section, anterior surface 204 may mirror posterior surface 206 about a center line of capsular ring 200), a particular orientation within the capsular bag 108 may not be necessary.

In certain embodiments, exterior surface 208 may comprise a generally concave surface configured such that, when positioned in the capsular bag 108 of a patient's eye, an equatorial void is created around the equatorial region 114 of the capsular bag 108 (as described in detail below with regard to FIGS. 4A-4B). Although depicted and primarily described as a concave surface, the present disclosure contemplates that exterior surface 208 may comprise any suitable shape such that, when positioned in the capsular bag 108 of a patient's eye, an equatorial void is created around the equatorial region 114 of the capsular bag 108. For example, exterior surface 208 may comprise a square or rectangular shape with corners that engage the capsular bag 108 such that an equatorial void is created around the equatorial region 114 of the capsular bag 108. As another example, exterior surface 208 may comprise a convex shape extending between corners that engage the capsular bag 108 such that an equatorial void is created around the equatorial region 114 of the capsular bag 108.

In certain embodiments, interior surface 210 may comprise a generally concave surface that corresponds to the shape of a haptic of a lens portion of the IOL such that, when the capsular ring 200 is positioned in the capsular bag 108 of a patient's eye, a lens portion of the IOL may be seated in the capsular ring 200 by engaging with interior surface 210 (as described in detail below with regard to FIGS. 4A-4B). Although depicted and primarily described as a concave surface, the present disclosure contemplates that interior surface 210 may comprise any suitable shape configured to receive a haptic of a lens portion of the IOL such that the lens portion of the IOL may be seated in the capsular ring 200 by engaging with interior surface 210. For example, interior surface 210 may comprise a square or rectangular shaped region configured to receive a haptic of a lens portion of the IOL having a corresponding shape.

In certain embodiments, anterior surface 204 and posterior surface 206 may each comprise one or more flaps 212. Flaps 212 may generally comprise structures extending outwardly from capsular ring 200 and defined by two surfaces intersecting at an acute angle. As a result, when capsular ring 200 is positioned in the capsular bag 108 of a patient's eye, the flaps 212 may interact with the capsular bag 108 in a manner that inhibits migration of epithelial cells (as described in detail below with regard to FIGS. 4A-4B). For example, flaps 212 may be flexible and may interact with the capsular bag 108 by creating localized areas of pressure on the capsular bag 108. Although anterior surface 204 and posterior surface 206 are each depicted as having a particular number of flaps 212 having a particular shape, the presented disclosure contemplates that anterior surface 204 and posterior surface 206 may each have any suitable number of flaps 212 having any suitable shape.

Capsular ring 200 may be constructed from a structurally deformable biocompatible material or combination of such materials, enabling capsular ring 200 to elastically or plastically deform without compromising its integrity. For example, capsular ring 200 may be made from a resilient polymer, such as silicone or 2-phenyl ethyl acrylate and 2-pheylethyl methacrylate known under the name AcrySof®. Other materials having shape memory characteristics may also be used. In certain embodiments, the material composition of capsular ring 200 resiliently biases the ring towards the expanded condition. Moreover, the capsular ring 200 may be sized such that, when implanted in the capsular bag 108, such biasing exerts pressure on the capsular bag 108.

Figure 3:
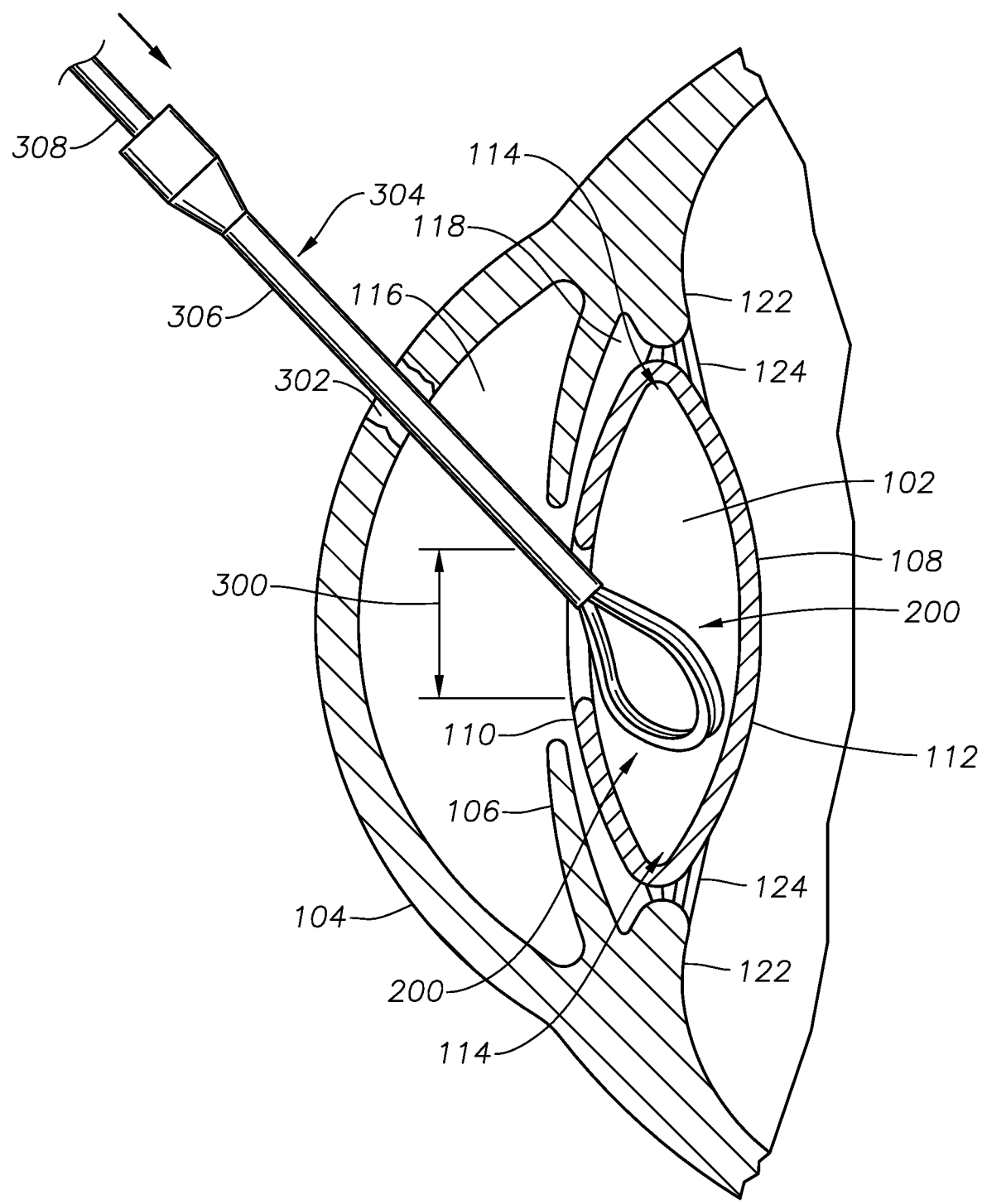
FIG. 3 illustrates an example mechanism for inserting the capsular ring depicted in FIGS. 2A-2B into the capsular bag of a patient's eye, according to certain embodiments of the present disclosure.

The above-discussed structurally deformable materials may allow capsular ring 200 to be restrained in a low profile configuration during delivery into the eye and to resume and maintain its expanded shape in vivo after the delivery process. For example, FIG. 3 illustrates an example mechanism for inserting capsular ring 200 into the capsular bag 108 of a patient's eye 100, according to certain embodiments of the present disclosure. The capsular bag 108 of eye 100 is shown with an anterior capsulorhexis 300 (i.e., an area of the anterior capsule 110 that has been removed) and with the natural lens removed. As a result, an incision 302 in the cornea 104 may allow for the insertion of capsular ring 200 into capsular bag 108 via incision 302 and anterior capsulorhexis 300.

In certain embodiments, capsular ring 200 may be inserted into the capsular bag 108 of a patient's eye 100 using a delivery instrument 304. A lumen 306 of delivery instrument 304 may be inserted through corneal incision 302 (e.g., a 1.5-4 mm incision), through anterior capsulorhexis 300, and into the capsular bag 108. Capsular ring 200 may be housed in the lumen 306 in a compressed (i.e., unexpanded) state. Delivery instrument 304 may include a plunger 308 configured to translate longitudinally within lumen 306 such that plunger 308 may push capsular ring 200 out of the distal end of lumen 306 and into capsular bag 108. Upon exiting the distal end of lumen 306 of delivery instrument 304, capsular ring 200 may assume the expanded position and may be located along the equatorial region 114 of capsular bag 108.

Although a particular technique for inserting capsular ring 200 into the capsular bag 108 of a patient's eye 100 has been described, the present disclosure contemplates that capsular ring 200 may be inserted into the capsular bag 108 of a patient's eye 100 using any suitable technique, according to particular needs.

Figure 4A:
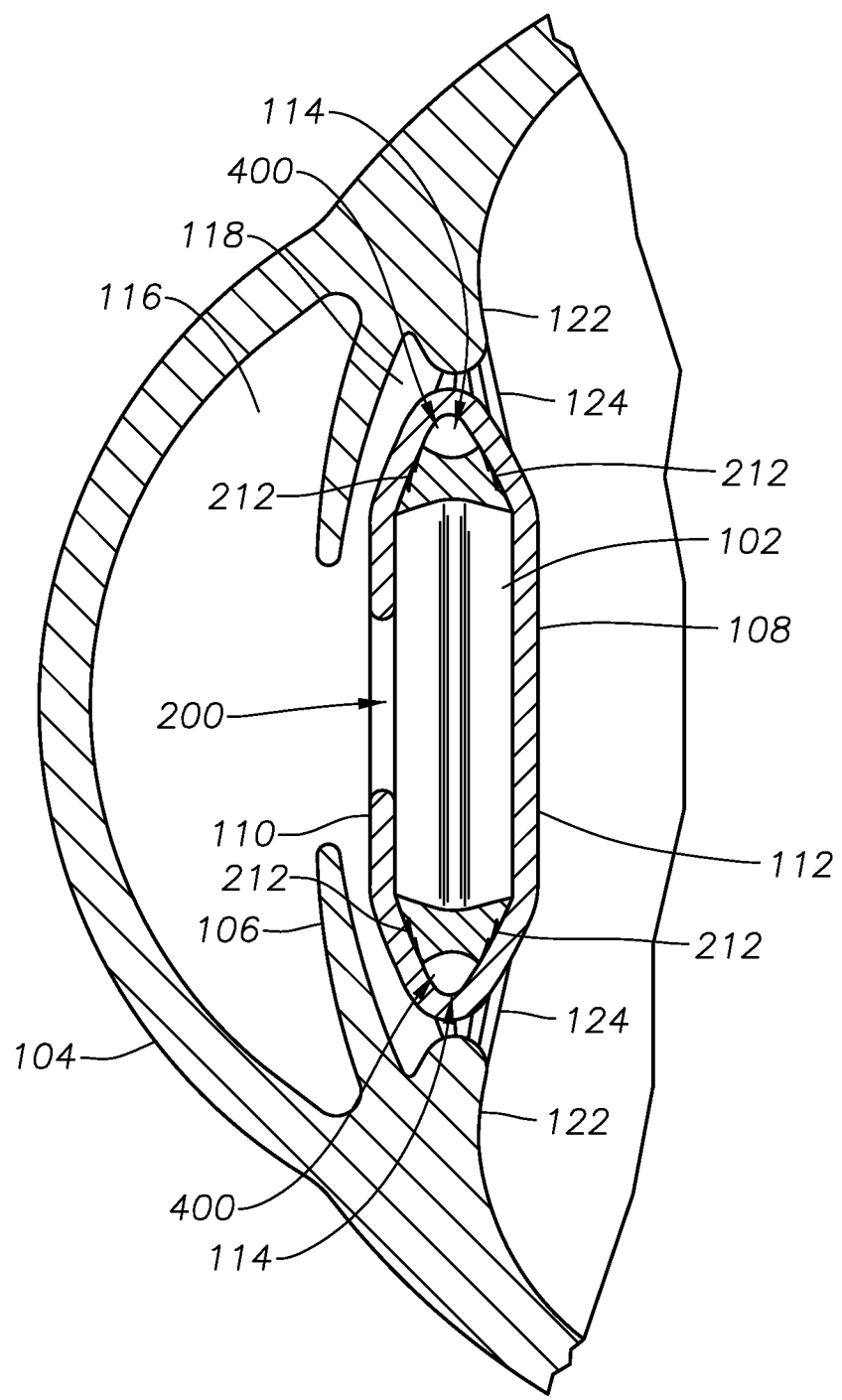
FIGS. 4A-4B illustrate a cross-section of the capsular ring depicted in FIGS. 2A-2B after insertion into the capsular bag of a patient's eye, according to certain embodiments of the present disclosure.
Figure 4B:
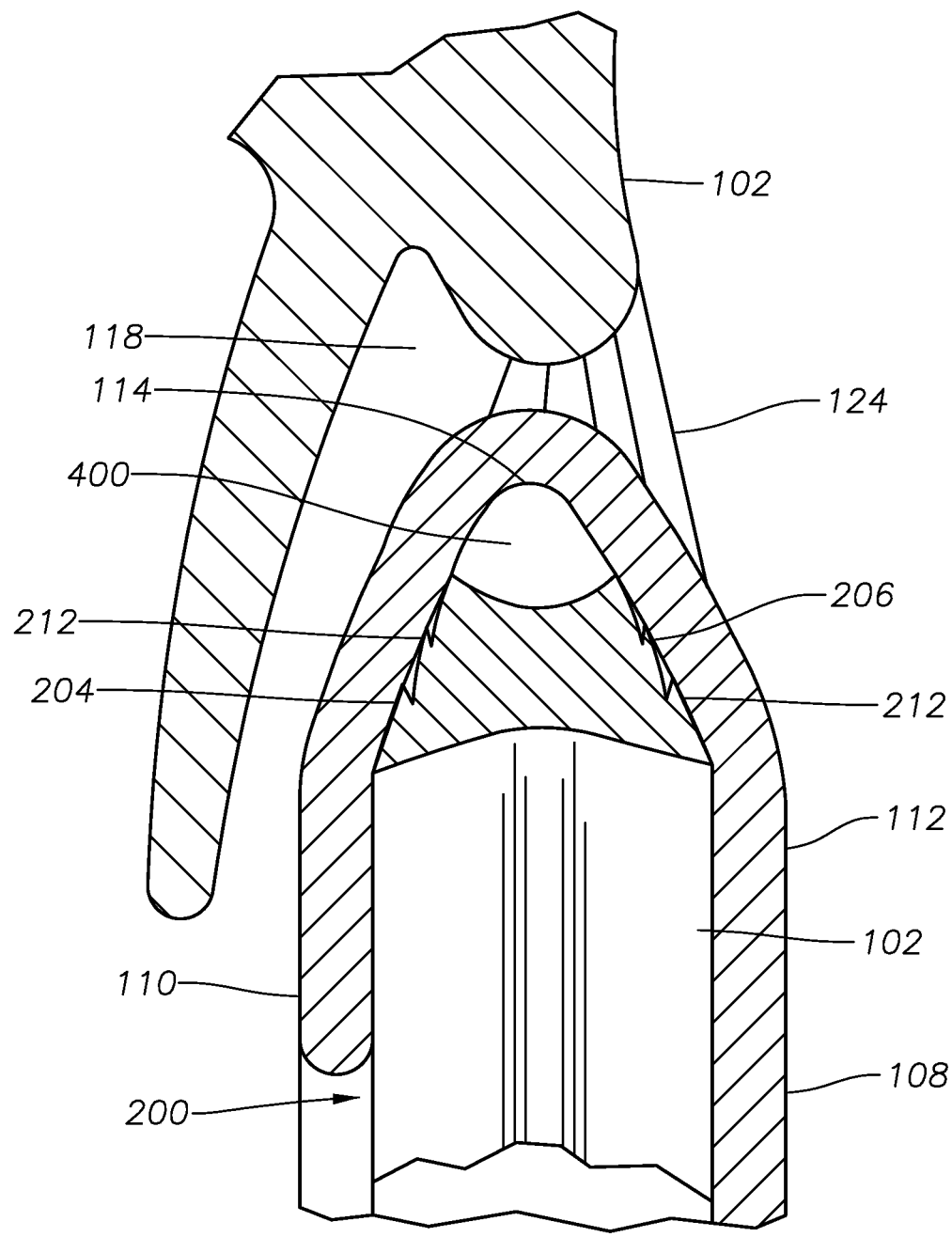

FIGS. 4A-4B illustrate a cross-section of capsular ring 200 after insertion into the capsular bag 108 of a patient's eye 100, according to certain embodiments of the present disclosure. When positioned along the equatorial region 114 of capsular bag 108, capsular ring 200 may maintain separation between anterior capsule 110 and posterior capsule 112. In other words, capsular ring 200 may keep capsular bag 108 open. As a result, aqueous humor located in the anterior chamber 116 may be allowed to circulate through capsular bag 108 by passing through anterior capsulorhexis 300. This circulation may help to prevent migration of lens epithelial cells, thus reducing the likelihood of PCO.

In addition to keeping capsular bag 108 open, concave exterior surface 208 of capsular ring 200 may create an equatorial void 400 when seated along the equatorial region 114 of the capsular bag 108. Additionally, equatorial void 400 may be bounded by the sharp transitions between concave exterior surface 208 and anterior surface 204/posterior surface 206 engaging the capsular bag 108, and these sharp transitions may help prevent the migration of lens epithelial cells from the equatorial region 114 to other areas of the capsular bag 108. In other words, the equatorial void 400 may serve to contain lens epithelial cells, thereby reducing the likelihood of PCO.

Additionally, the one or more flaps 212 located on the anterior surface 204 of capsular ring 200 may interface with anterior capsule 110. Similarly, the one or more flaps 212 located on the posterior surface 206 of capsular ring 200 may interface with posterior capsule 112. Like the sharp transitions between concave exterior surface 208 and anterior surface 204/posterior surface 206 discussed above, the acute angles of flaps 212 may further help to prevent migration of lens epithelial cells (e.g., those lens epithelial cells escaping equatorial region 114). As a result, flaps 212 may provide an additional impediment to lens epithelial cell migration, thereby further reducing the likelihood of PCO.

Figure 5A:
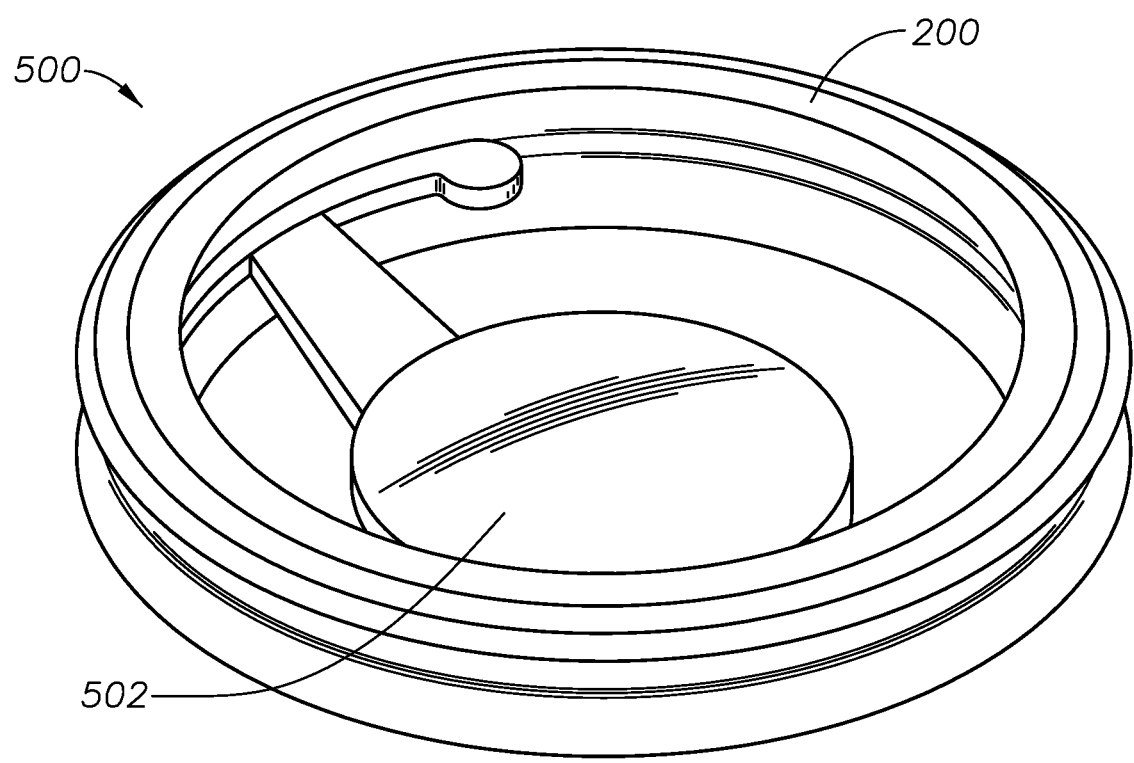
FIGS. 5A-5B illustrate an example IOL system including the capsular ring depicted in FIGS. 2A-2B, according to certain embodiments of the present disclosure.
Figure 5B:
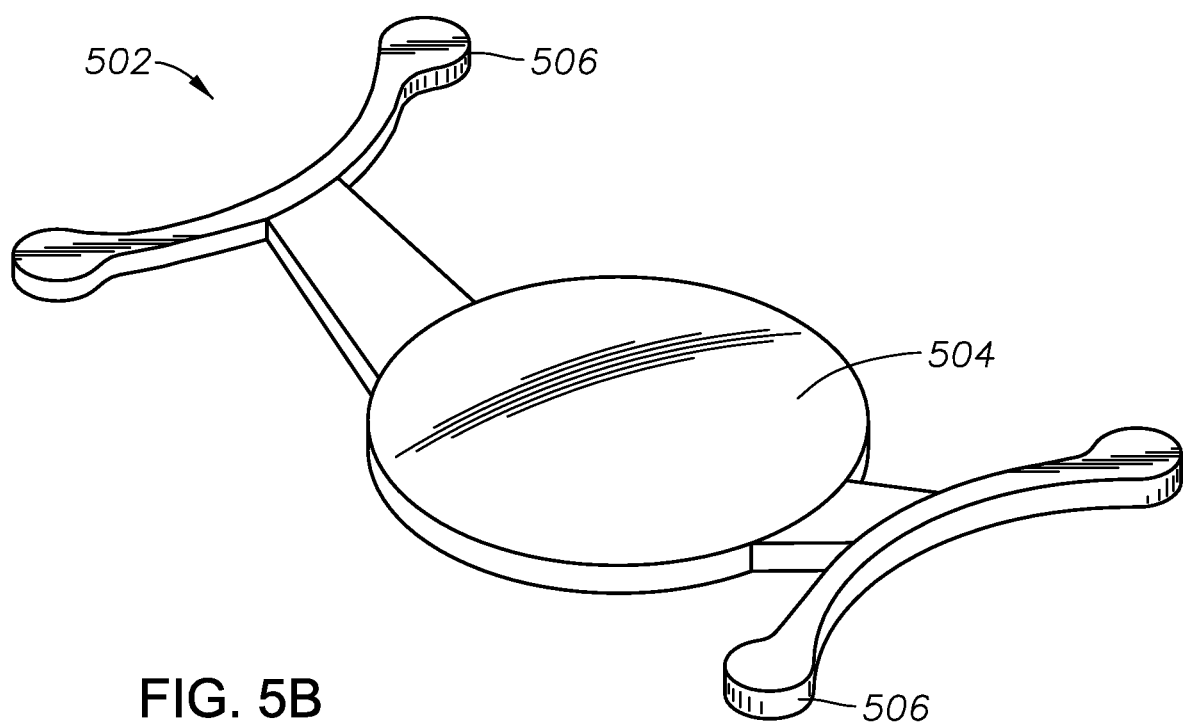

FIGS. 5A-5B illustrate an example IOL system 500 including capsular ring 200, according to certain embodiments of the present disclosure. In addition to the capsular ring 200, IOL system 500 may include a lens 502 configured to interface with capsular ring 200. For example, as illustrated in FIG. 5B, lens 502 may include an optic 504 (e.g., any suitable optic for correcting a patient's vision) and one or more haptics 506. Haptics 506 may be configured to interface with interior surface 210 of capsular ring 200 such that, after capsular ring 200 is inserted into the capsular bag 108 of a patient's eye 100, lens 502 may be seated in capsular ring 200 (via haptics 506 engaging interior surface 210) and optic 504 may lie along the visual axis of the patient's eye 100.

In certain embodiments, the haptics 506 may be configured such that, when lens 502 is seated in capsular ring 200, the optic 504 is positioned in a plane located posterior to the plane of the capsular ring 200. As a result, the lens 502 may engage the posterior capsule 112, thereby aiding capsular ring 200 in maintaining an open capsular bag 108.

Although a particular number of haptics 506 having a particular shape are depicted, the present disclosure contemplates that lens 502 may include any suitable number of haptics having any suitable configuration facilitating the above-described use of lens 502 in conjunction with capsular ring 200.

Figure 6:
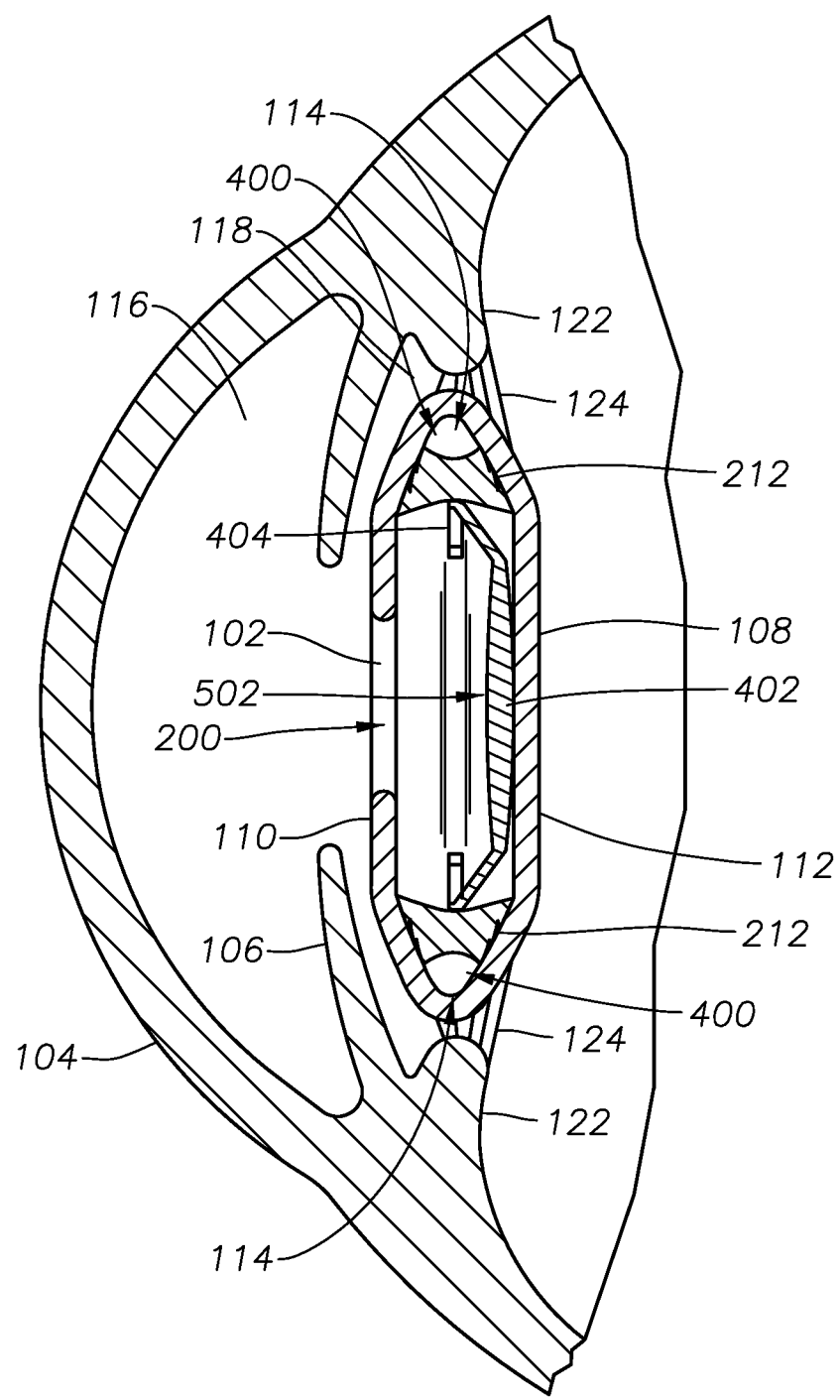
FIG. 6 illustrates the IOL system depicted in FIGS. 5A-5B after insertion into the capsular bag of a patient's eye, according to certain embodiments of the present disclosure.

FIG. 6 illustrates IOL system depicted in FIGS. 5A-5B after insertion into the capsular bag of a patient's eye, according to certain embodiments of the present disclosure. As discussed above, the haptics 506 being configured such that the optic 504 is positioned in a plane located posterior to the plane of the capsular ring 200 may cause the lens 502 to contact the posterior capsule 112. Additionally, the lens 502 may exert pressure on the posterior capsule 112. As a result, posterior capsule 112 may be prevented from moving toward anterior capsule 110, thus aiding capsular ring 200 in maintaining an open capsular bag 108.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A capsular ring for insertion into a capsular bag of a patient's eye, the capsular ring comprising:
    a concave exterior surface extending continuously around an entire circumference of the capsular ring and configured, upon insertion into the capsular bag of the patient's eye, to engage an equatorial region of the capsular bag of the patient's eye, the concave exterior surface extending between an anterior surface of the capsular ring and a posterior surface of the capsular ring;

a concave interior surface extending from the anterior surface to the posterior surface, the interior surface configured for one or more haptics of a lens to engage the interior surface;

a first one or more flaps arranged on the anterior surface, each of the first one or more flaps extending at least partially away from the anterior surface and being defined by two surfaces intersecting at an acute angle, at least a portion of each of the first one or more flaps configured, upon insertion into the capsular bag of the patient's eye, to engage an anterior portion of the capsular bag of the patient's eye; and a second one or more flaps arranged on the posterior surface, each of the second one or more flaps extending at least partially away from the posterior surface and being defined by two surfaces intersecting at an acute angle, at least a portion of each of the second one or more flaps configured, upon insertion into the capsular bag of the patient's eye, to engage a posterior portion of the capsular bag of the patient's eye;

wherein each of the surfaces defining the one or more flaps extends radially outwardly with respect to an interior area defined by the interior surface of the capsular ring.

2. The capsular ring of claim 1, wherein at least a portion of the capsular ring is constructed from a structurally deformable, biocompatible material.

3. The capsular ring of claim 1, wherein the concave exterior surface defines an outer diameter of the capsular ring, the outer diameter corresponding to a diameter of the equatorial region of the capsular bag of the patient's eye.

4. The capsular ring of claim 1, further comprising the lens, the lens configured such that, when the one or more haptics of the lens are engaged with the interior surface, an optic of the lens is positioned in a first plane corresponding to a posterior surface of the optic and the capsular ring is positioned in a second plane corresponding to the posterior surface of the capsular ring, the second plane being parallel to the first plane.

5. The capsular ring of claim 4, wherein the lens is further configured such that, when the lens and the capsular ring are located in the capsular bag of the patient's eye, the first plane is posterior to the second plane such that the lens makes contact with and exerts pressure on a posterior surface of the capsular bag of the patient's eye.

6. An intra-ocular lens (IOL) system, comprising:

a capsular ring for insertion into a capsular bag of a patient's eye, the capsular ring comprising:

a concave exterior surface extending continuously around an entire circumference of the capsular ring and configured, upon insertion into the capsular bag of the patient's eye, to engage an equatorial region of the capsular bag of the patient's eye, the concave exterior surface extending between an anterior surface of the capsular ring and a posterior surface of the capsular ring;

a first one or more flaps arranged on the anterior surface, each of the first one or more flaps extending at least partially away from the anterior surface and being defined by two surfaces intersecting at an acute angle, at least a portion of each of the first one or more flaps configured, upon insertion into the capsular bag of the patient's eye, to engage an anterior portion of the capsular bag of the patient's eye; and a second one or more flaps arranged on the posterior surface, each of the second one or more flaps extending at least partially away from the posterior surface and being defined by two surfaces intersecting at an acute angle, at least a portion of each of the second one or more flaps configured, upon insertion into the capsular bag of the patient's eye, to engage a posterior portion of the capsular bag of the patient's eye;

wherein each of the surfaces defining the one or more flaps extends radially outwardly with respect to an interior area defined by an interior surface of the capsular ring;

wherein the interior surface is concave and extends between the anterior surface of the capsular ring and the posterior surface of the capsular ring;

a lens comprising an optic and one or more haptics, the lens configured to be seated in the capsular ring when the one or more haptics engage the interior surface of the capsular ring.

7. The intra-ocular lens (IOL) system of claim 6, wherein at least a portion of the capsular ring is constructed from a structurally deformable biocompatible material.

8. The intra-ocular lens (IOL) system of claim 6, wherein the concave exterior surface defines an outer diameter of the capsular ring, the outer diameter corresponding to a diameter of the equatorial region of the capsular bag of the patient's eye.

9. The intra-ocular lens (IOL) system of claim 6, wherein the lens is configured such that, when seated in the capsular ring, the optic is located in a first plane corresponding to a posterior surface of the optic and the capsular ring is located in a second plane corresponding to the posterior surface of the capsular ring, the second plane being parallel to the first plane.

10. The intra-ocular lens (IOL) system of claim 9, wherein the lens is further configured such that, when the lens and the capsular ring are located in the capsular bag of the patient's eye, the first plane is posterior to the second plane such that the lens makes contact with and exerts pressure on a posterior surface of the capsular bag of the patient's eye.

11. An intra-ocular lens (IOL) system, comprising:

a capsular ring comprising:

an exterior surface extending continuously around an entire circumference of the capsular ring and configured, upon insertion into a capsular bag of a patient's eye, to engage an equatorial region of the capsular bag of the patient's eye, the exterior surface extending between an anterior surface of the capsular ring and a posterior surface of the capsular ring;

an interior surface extending between the anterior surface of the capsular ring and the posterior surface of the capsular ring;

one or more posterior flaps arranged on the posterior surface, each of the one or more posterior flaps extending at least partially away from the posterior surface and being defined by two surfaces intersecting at an acute angle, at least a portion of each of the one or more posterior flaps configured, upon insertion into the capsular bag of the patient's eye, to engage a posterior portion of the capsular bag of the patient's eye;

one or more anterior flaps arranged on the anterior surface of the capsular ring, each of the one or more anterior flaps extending at least partially away from the anterior surface and being defined by two surfaces intersecting at an acute angle, at least a portion of each of the one or more anterior flaps configured, upon insertion into the capsular bag of the patient's eye, to engage an anterior portion of the capsular bag of the patient's eye;

wherein each of the surfaces defining the one or more posterior and anterior flaps extends radially outwardly with respect to an interior area defined by the interior surface of the capsular ring;

a lens comprising an optic and one or more haptics, the lens configured to be seated in the capsular ring when the one or more haptics engage the interior surface of the capsular ring;

wherein the capsular ring and the lens are configured such that, when the lens is seated in the capsular ring, a first plane corresponding to a posterior surface of the optic is situated posterior to a second plane corresponding to the posterior surface of the capsular ring and, when implanted, the optic makes contact with and exerts pressure on a posterior surface of the capsular bag of the patient's eye.

12. The IOL system of claim 11, wherein the exterior surface is concave.

* * * * *